United States Patent [19]

Hancock et al.

[11] Patent Number: 5,367,032

[45] Date of Patent: Nov. 22, 1994

[54] PROCESS FOR THE PRODUCTION OF CARBONYL-CONTAINING COMPOUNDS FROM EPOXIDES

[75] Inventors: David A. Hancock; David J. Moreton; Lee J. Morton, all of Hull, England

[73] Assignee: BP Chemicals Limited, London, England

[21] Appl. No.: 180,076

[22] Filed: Jan. 11, 1994

[30] Foreign Application Priority Data

Jan. 15, 1993 [GB] United Kingdom ............... 9300739

[51] Int. Cl.$^5$ ........................... C08F 8/06; C08F 8/08
[52] U.S. Cl. ............................. 525/333.8; 525/340; 568/404; 568/405; 568/485; 568/486
[58] Field of Search ................. 525/340, 333.8; 568/404, 405, 485, 486

[56] References Cited

U.S. PATENT DOCUMENTS

| | | | |
|---|---|---|---|
| 3,931,024 | 1/1976 | Hu | 252/51.5 R |
| 4,925,986 | 5/1990 | Monnier et al. | 568/450 |
| 5,015,697 | 5/1991 | Riddick | 525/333.8 |
| 5,028,666 | 7/1991 | Clarke | 525/388 |
| 5,032,323 | 7/1991 | Virnig | 568/384 |
| 5,034,471 | 7/1991 | Blackborow | 525/333.8 |
| 5,245,062 | 9/1993 | Stoll et al. | 560/174 |

FOREIGN PATENT DOCUMENTS

| | | |
|---|---|---|
| 0385039 | 9/1990 | European Pat. Off. . |
| 4001316 | 7/1991 | Germany . |
| 1172818 | 12/1969 | United Kingdom . |
| 2055821 | 3/1981 | United Kingdom . |

*Primary Examiner*—Robert E. Sellers
*Attorney, Agent, or Firm*—Brooks Haidt Haffner & Delahunty

[57] ABSTRACT

Epoxides are converted selectively to the corresponding carbonyl-containing compounds by reacting the epoxide with an oxidizing agent, typically hydrogen peroxide, in a liquid aqueous/organic two-phase system comprising:

(a) an organic phase substantially containing the epoxide, and (b) an aqueous acidic phase substantially containing the oxidizing agent, in the presence of an onium compound capable of achieving phase partitioning and a catalytic system comprising a first catalyst component which is at least one element selected from tungsten, molybdenum, vanadium and chromium, or a compound containing at least one of the aforesaid elements, and a second catalyst component which is a phosphorus (V) acid or a species convertible to a phosphorus (V) acid.

8 Claims, No Drawings

PROCESS FOR THE PRODUCTION OF CARBONYL-CONTAINING COMPOUNDS FROM EPOXIDES

The present invention relates in general to a process for the production of carbonyl-containing compounds from epoxides. In particular the invention relates to the production of carbonyl-containing compounds, suitable for use as intermediates in the production of fuel and lubricating oil additives, from epoxides derived *from olefinically unsaturated polyolefins, hereinafter to be referred to as polyolefinic epoxides, containing upwards of 30 carbon atoms.

The formation of ketones by the rearrangements of epoxides is well known. DE-A-4001316, for example, discloses a process for preparing ketone compounds by the rearrangement of epoxides in the presence of iodide ions, in which quaternary ammonium and phosphonium salts, which may be mixed with alkali metal iodides, are used as rearrangement catalysts. The rearrangement is accomplished at temperatures in the range from 160° to 230° C.

Moreover, EP-A-385039 discloses a process for producing active carbonyl compounds predominating in aldehyde groups from polybutenes having at least 50% of the unsaturation in the terminal position, the process comprising:
 (a) epoxidising the polybutene in the liquid phase with a peroxygen compound or a compound capable of giving rise to a peroxygen compound under the reaction conditions, and
 (b) isomerising the epoxide formed from step (a) to the corresponding carbonyl compound.

It is also known to produce epoxides by the catalytic epoxidation of olefins by hydrogen peroxide in a liquid aqueous/organic two phase system which comprises (a) an organic phase substantially containing the olefinically unsaturated compound and (b) an aqueous acidic phase substantially containing the hydrogen peroxide in the presence of an onium salt and a catalytic system comprising a first catalytic component which is at least one first element or a derivative thereof selected from tungsten, molybdenum and vanadium, and a second catalyst component which is at least one derivative of phosphorus or arsenic. Such a reaction is known from GB-A-2055821 and from C. Venturello, E. Alueri and M. Ricci, J. Org. Chem., 1983, 48,3831–3833; O. Bortolini, F. Di Furia, G. Modena and R. Seraglia, J. Org. Chem., 1985, 50,2688–2690; and C. Venturello and R. D'Aloisio, J. Org. Chem., 1988, 53, 1553–1557. Although various references are made in these documents to the acid-catalysed hydrolytic cleavage of the oxirane ring to diol, there is no mention so far as can be ascetained of the formation of carbonyl-containing compounds.

According to the present invention, epoxides are converted to the corresponding carbonyl-containing compounds, for example ketones and/or aldehydes, by a process which comprises reacting the epoxide with an oxidising agent in a liquid aqueous/organic two-phase system, which system comprises (a) an organic phase substantially containing the epoxide and (b) an aqueous acidic phase substantially containing the oxidising agent, in the presence of an onium compound capable of achieving phase partitioning and a catalytic system comprising a first catalyst component which is at least one element selected from tungsten, molybdenum, vanadium and chromium, or a compound containing at least one of the aforesaid elements, and a second catalyst component which is a phosphorus (V) acid or a species convertible to a phosphorus (V) acid.

An epoxide within the context of the present invention is one containing at least one oxirane group and at least two carbon atoms, at least one of the substituents of the oxirane group being a hydrogen atom. Any such epoxide may be used in the process of the invention. Thus, the epoxide may suitably be one produced by the process as described in GB-A-2055821, i.e. one produced by epoxidation of an olefin having the formula:

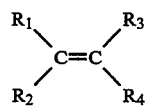

wherein $R_1$, $R_2$, $R_3$ and $R_4$, optionally substituted with functional groups inert to the reaction conditions, each represent a hydrogen atom or a hydrocarbyl group such as an alkyl or alkenyl group having up to 30 carbon atoms, a cycloalkyl or cycloalkenyl group having from 3 to 12 carbon atoms, optionally branched, or an aryl, alkyl-aryl or alkenyl-aryl group having from 6 to 12 carbon atoms, or $R_1$, $R_2$, $R_3$ and $R_4$ taken together with an adjacent group represents an alkyl or alkenyl group having from 1 to 12 carbon atoms in the resulting cycle. The epoxide may also be any of the epoxides described in DE-A-4001316 i.e. (a) epoxides of aliphatic or cycloaliphatic monoolefins having 6 to 30 carbon atoms, (b) epoxides of esters of unsaturated fatty acids having 11 to 22 carbon atoms and 1, 2 or 3 double bonds with linear or branched aliphatic, saturated or unsaturated alcohols having 1 to 22 carbon atoms and 0,1, 2 or 3 double bonds, araliphatic alcohols having 7 to 15 carbon atoms or phenols, (C) epoxides of esters of unsaturated fatty acids with polyols, (d) epoxides of esters of saturated aliphatic carboxylic acids having 1 to 22 carbon atoms with aliphatic unsaturated alcohols having 1 to 22 carbon atoms and 1, 2 or 3 double bonds, and (e) epoxides of alkenyl ethers and alkenyl(poly)-alkylene glycol ethers having an alkenyl group having 11 to 22 carbon atoms and 1, 2 or 3 double bonds and a further linear or branched alkyl or alkenyl group having 1 to 22 carbon atoms, an aralkyl group having 7 to 15 carbon atoms or a phenyl group.

A preferred epoxide is a polyolefinic epoxide containing upwards of 30 carbon atoms such as may be obtained by the epoxidation of an olefinically unsaturated polyolefin having greater than 30 carbon atoms. The olefinic unsaturation may be in the backbone chain or a side chain of the unsaturated polyolefin, and may be internal or terminal. A preferred olefinically unsaturated polyolefin is a polyisobutene. Preferred polyisobutenes are those known as highly reactive polyisobutenes, that is polyisobutenes wherein, greater than 50% for example greater than 70%, typically greater than 85%, of the residual olefinic double bonds, are of the vinylidene type, ie represented by the formula:

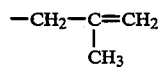

Such polyisobutenes are also known as high vinylidene polyisobutenes. Highly reactive polyisobutenes are commercially available in the form of ULTRAVIS (RTM) polyisobutenes from BP Chemicals Limited and GLISSOPAL (RTM) from BASF. The polyolefinic epoxide may suitably be prepared by the catalytic reaction of an olefinically unsaturated compound with hydrogen peroxide in a liquid aqueous/organic two-phase system, which system comprises:

(a) an organic phase substantially containing the olefinically unsaturated compound, and (b) an aqueous acidic phase substantially containing the hydrogen peroxide, in the presence of an onium compound and a catalytic system comprising a first catalytic component which is at least one first element selected from tungsten, molybdenum and vanadium, or a compound containing the first element, and a second catalyst component which is a phosphorus (V) acid or a species convertible to a phosphorus (V) acid.

As the oxidising agent there may be used either hydrogen peroxide, nitric acid or potassium dichromate, for example. A particularly preferred oxidising agent is hydrogen peroxide, which is commercially available in the form of aqueous solutions of differing strengths. Typically, it will be found convenient to use 8% aqueous hydrogen peroxide, though a 35% solution may be used if desired. Although the oxidising agent may be added in a single addition at the start of the reaction, it is very much preferred to add it in a plurality of discrete additions or continuously throughout the reaction. In the case of aqueous hydrogen peroxide for example it may be added in greater than 3, preferably greater than 5 aliquots. Alternatively it may be added as a drip, either intermittently or continuously, or as a continuous stream throughout the reaction.

The reaction is carried out in a liquid aqueous/organic two-phase system. The system comprises (a) an organic phase substantially containing the epoxide. Suitably the organic phase can be any organic liquid inert with respect to the reactants. Suitable such organic liquids include aliphatic, alicyclic and aromatic hydrocarbons, for example toluene, benzene, xylene, octane and cyclohexane, and chlorinated hydrocarbons, such as the chloroalkanes, though the latter are less preferred for environmental reasons. The system further comprises (b) an aqueous acidic phase substantially containing the hydrogen peroxide. The aqueous phase may be rendered acidic by the addition of a suitable acid. Suitably the pH of the aqueous phase may be rendered less than 7, typically from 0 to 2, for example 0.4 to 1.5, by the addition of an acid, for example sulphuric acid, phosphoric acid, nitric acid, chromic acid or hydrochloric acid. Alternatively, there may be employed an acid as hereinbefore described supported on a suitable support, for example a clay or a zeolite, for example FULMONT XMP3 (a sulphuric acid activated clay). It is an advantage of the invention that the conversion of polyisobutene epoxides, for example, to carbonyl-containing compounds can be profoundly influenced by the choice of acid used for adjusting the pH of the aqueous phase. Thus, using sulphuric acid for pH adjustment and a polyisobutene epoxide having a high proportion of terminal epoxide groups, for example an ULTRAVIS polyisobutene epoxide, aldehydic carbonyl groups are preferentially formed. Using phosphoric acid for pH adjustment and a polyisobutene epoxide, keto carbonyl groups are preferentially formed.

The two-phase system is well-known in the art, it generally being referred to as a phase transfer system. Execution of a phase transfer process depends on efficient stirring, which may be achieved by any suitable means known in the art, and the use of a phase transfer catalyst, which in this system is any onium compound capable of achieving phase partitioning. Suitable onium compounds are those having the formula:

$$(R^1, R^2, R^3, R^4 M)^+ X^- \quad (I)$$

wherein M is a pentavalent element belonging to Group VA of the Periodic Table, which is either nitrogen, phosphorus, arsenic or antimony, preferably nitrogen or phosphorus, $X^-$ is a stable anion, such as a halide, for example $Cl^-$ or $Br^-$, and $R^1$, $R^2$, $R^3$ and $R^4$ are independently hydrocarbyl groups of a chain length sufficient to achieve partitioning or phase transfer. Preferred hydrocarbyl groups are alkyl groups. Suitably the total number of carbon atoms in the groups $R^1$, $R^2$, $R^3$ and $R^4$ is greater than 25. An example of a suitable onium salt having the formula (I) is tricetylmethylammonium chloride.

The catalytic system comprises a first catalytic component which is at least one first element selected from tungsten, molybdenum, vanadium and chromium, or a compound containing the element. Compounds considered to be particularly effective are tungstic, molybdic and vanadic acids and their corresponding alkali or alkaline earth metal salts, especially the salts, which can be neutral or acidic salts. Of the metals tungsten, molybdenum, vanadium and chromium, tungsten and molybdenum are preferred and tungsten is more preferred. An example of a particularly suitable first component is sodium tungstate. There may however be used, for example, the metal carbonyls, the metal oxides, the metal carboxylates, for example naphthenates and stearates, and the like. As a second component the catalytic system comprises a phosphorus (V) acid or a species convertible under the reaction conditions to a phosphorus (V) acid. Preferred second components include phosphoric acid.

The two or more catalyst components used in the process may belong to different molecules or they may both be incorporated into a single compound, for example a phosphotungstic acid.

The relative composition of the reaction mixture will be described by way of illustration with particular regard to hydrogen peroxide as the oxidising agent. The concentration of hydrogen peroxide in the aqueous layer should not at any time exceed the safety limits, typically a maximum of about 20% by weight should be adhered to. The total amount of hydrogen peroxide added relative to the epoxide is suitably in the range from 0.4 to 5 molar equivalents per equivalent of the epoxide.

As regards the ratio of organic phase to aqueous phase in the two-phase system there may suitably be used a volume ratio of organic phase to aqueous phase in the range from 10:1 to 1:1, typically 2.5:1.

The onium compound may suitably by present in an amount from 0.01 to 0.4, preferably from 0.02 to 0.05, molar equivalents per molar equivalent of epoxide.

The amount of the first catalytic component may suitably be in the range from 0.01 to 0.5, preferably from 0.06 to 0.1 molar equivalents per molar equivalent of epoxide.

The amount of the phosphorus (V) acid comprising the second component of the catalyst is suitably between 0.025 and 0.5, preferably between 0.04 and 0.15 molar equivalents per mole of epoxide.

The reaction of the epoxide with hydrogen peroxide for example as the oxidising agent may suitably be effected at elevated temperature, the upper limit of which is dictated by the temperature at which hydrogen peroxide decomposes. Temperatures in the range from 50° to 100° C., preferably from 70° to 95° C. typically about 90° C., may be employed.

In a particularly preferred embodiment the present invention provides a method for converting an olefinically unsaturated compound to a carbonyl-containing compound, for example an aldehyde or a ketone, without isolating any intermediate compound.

Accordingly the present invention provides a process for the production of a carbonyl-containing compound from an olefinically unsaturated compound which process comprises the steps of:

(I) reacting the olefinically unsaturated compound with hydrogen peroxide in a liquid aqueous/organic two-phase system, which system comprises (a) an organic phase substantially containing the olefinically unsaturated compound and (b) an aqueous acidic phase substantially containing the hydrogen peroxide in the presence of an onium compound capable of achieving phase partitioning and a catalytic system comprising a first catalytic component which is at least one element selected from tungsten, molybdenum and vanadium, or a compound containing the element and a second catalyst component which is a phosphorus (V) acid or a species convertible to a phosphorus (V) acid, thereby to form the corresponding epoxide, and (II) without isolating the epoxide product of step (I) from the reaction mixture, acidifying the mixture and adding an oxidising agent, thereby to convert the epoxide to a carbonyl-containing compound.

As regards step (I) of the process the liquid aqueous/organic two-phase system, hydrogen peroxide, the onium compound and the catalytic system are as hereinbefore described with reference to the process for converting an epoxide to a carbonyl-containing compound. The hydrogen peroxide may be added in a single addition at the beginning of the reaction but for optimum results it is very much preferred to add it in a plurality of discrete additions or continuously throughout the reaction. Suitably the hydrogen peroxide may be added in greater than 3, preferably greater than 5 aliquots. Alternatively, it may be added as a drip or as a continuous stream throughout the reaction.

Suitably the pH of the aqueous phase in step (I) may be rendered, by the addition of a suitable acid, in the range 0 to 7, preferably 0.5 to 4, more preferably 1 to 2. Suitable acids include, for example, sulphuric and phosphoric acids.

As the olefinically unsaturated compound there may be used an olefin as described in GB-A-2055821. Such olefins include, by way of example, alkyl, alicyclic and alkylaryl unsaturated hydrocarbons having up to 20 carbon atoms, such as propylene, butenes, pentenes, and in general the linear or branched mono- and di- olefins having up to 20 carbon atoms, cyclohexene, norbornene, limonene, camphene, vinyl-cyclohexene, stytens, indene and stilbene, unsaturated acids and their esters such as acrylic, methacrylic, crotonic and oleic acid, unsaturated alcohols and their esters such as allyl alcohol, and unsaturated aldehydes and ketones such as methylallyl acetone. Preferably however, the olefinically unsaturated compound may be an aliphatic olefinically unsaturated polyolefin containing greater than 30 carbon atoms, typically greater than 80 carbon atoms. The olefinic unsaturation may be in the main chain or the side chain of the unsaturated polyolefin, and may be internal or terminal. A preferred olefinically unsaturated polyolefin is a polyisobutene, more preferably a highly reactive polyisobutene as described hereinbefore. Functional group-containing unsaturated polyolefins may also be employed, for example those containing acrylate and methacrylate groups bond in the olefinically unsaturated compound.

As regards the ratio of organic phase to aqueous phase in the two-phase system there may suitably be used a volume ratio of organic phase to aqueous phase in the range from 10:1 to 1:1, typically 2.5:1.

The onium compound may suitably be present in an amount from 0.01 to 0.4, preferably from 0.02 to 0.05, molar equivalents per molar equivalent of double bond in the olefinically unsaturated compound.

The amount of the first catalytic component may suitably be in the range from 0.01 to 0.5, preferably from 0.06 to 0.1, molar equivalents per molar equivalent of double bond in the olefinically unsaturated compound.

The amount of the phosphorus (V) acid comprising the second component of the catalyst is suitably sufficient to provide the desired pH of the aqueous acidic phase.

The reaction of the olefinically unsaturated compound with the hydrogen peroxide may suitably be effected at elevated temperature, the upper limit being dictated by the temperature at which hydrogen peroxide decomposes. Temperatures from about 50° to 100° C., typically about 70° C. are preferred.

As regards step (II) of the process, this corresponds to the invention as hereinbefore described with reference to the conversion of an epoxide to a carbonyl-containing compound. In this embodiment of the invention the mixture from step (I) comprises the epoxide, the liquid aqueous/organic two-phase system, the onium compound and the catalytic system.

The only components to be added at this stage are the acid for the purpose of adjusting the pH in step (II) and the oxidising agent, which are as described hereinbefore with reference to the conversion of the epoxide to the carbonyl-containing compound.

The overall reaction starting with a vinylic polyisobutene may be represented as follows:

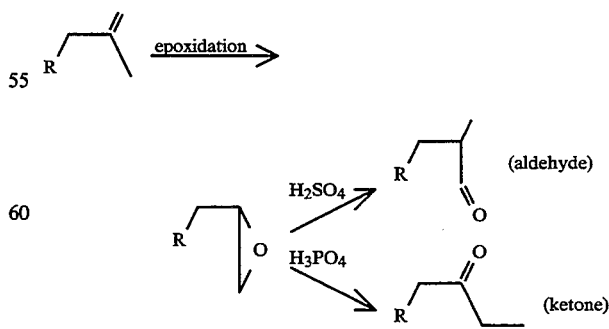

Carbonyl group-containing polyisobutenes produced by the process as aforesaid may be further reacted to produce materials useful as internal combustion engine fuels additives. Typically, they may be reacted with amines, in the presence or absence of formaldehyde, to produce nitrogen-containing materials.

The amine reactant useful in the production of additives may be any amine containing a reactive hydrogen atom. Preferred amines include the alkylene polyamines and the polyalkylene polyamines, for example diethylene triamine, triethylene tetramine, tetraethylene pentamine, dipropylene triamine and the like, dimethylamino propylamine (DMAPA) and polyalkoxyamines and aminoalkylalkanolamines, for example the commercially available Jeffamines (RTM). A suitable process for preparing an additive is described in for example US-A-3,931,024.

A preferred process for the production of a fuels additive comprises reacting the carbonyl-containing compound, preferably a carbonyl functionalised polyisobutene, with an amine and hydrogenating the product so-obtained in the manner described in EP-A-0382405 (BP Case No. ADD 7067), for example.

Optionally, the carbonyl-containing compounds resulting from the process of the present invention can be further oxidised to carboxylic acid derivatives, before conversion to nitrogen-containing additives, by the application of conventional oxidation methods. Such methods include for example nitric acid treatment of aldehyde-containing compounds and chromic acid treatment of ketone and/or aldehyde-containing compounds.

Nitrogen-containing polyisobutene additives obtained in the manner as aforesaid are particularly useful in fuels, e.g. spark ignition fuel, otherwise known as gasoline, or diesel fuels, and as lubricating oil additives, for example dispersants.

The invention will now be illustrated by reference to the following Examples. In the Examples the conversion to carbonyl species is determined by a Fourier transform Infra-red method.

EXAMPLE 1—Production of PIB aldehyde (i) production of epoxide intermediate

A 1 litre flask equipped with a thermocouple, condenser, overhead mechanical stirrer with PTFE blade and an addition port was charged with Ultravis 10 (a polyisobutene ex. BP Chemicals Limited) (240g; 0.24 mole), Arquad 316 (tricetylmethylammonium chloride) (4.16g; 5.04×10$^{-3}$ mole) and toluene (120g). A solution of sodium tungstate (6.59g; 0.199 mole) and water (15g) was prepared and the pH lowered to 1.0 using H$_3$PO$_4$ (40% w/w). This solution was added to the flask and the flask heated to 70° C. Aliquots (7) of hydrogen peroxide (8% w/w) were added at hourly intervals (7×14.9g=104.3g; 0.245 mole) whilst stirring.

(ii) Conversion of eposide intermediate to carbonyl-containing compounds

The aqueous layer containing the epoxide intermediate was separated off from the product of (i) above and its pH lowered to 1.0 by addition of sulphuric acid (30% w/w) (8g). The aqueous layer was then reintroduced to the 1 litre flask containing the organic layer and the reaction mixture heated to 70° C. Further aliquots (7) of hydrogen peroxide (8% w/w) (7×14.9g =104.3g; 0.245 mole) were added at hourly intervals. The organic layer was then separated, washed with water (three times), separated and dried over MgSO$_4$ and filtered through DIC filter aid. Finally the product was evaporated down at 80° C. and maximum vacuum (29 inches Hg) in a rotary evaporator. IR analysis confirmed by $^{13}$C and $^1$H NMR showed that PIB aldehyde had been selectively formed.

EXAMPLE 2—Preparation of PIB ketone (i) Production of epoxide intermediate

The epoxide intermediate was produced in a manner identical to that described in Example 1 (i) above.

(ii) Conversion of epoxide intermediate to carbonyl-containing compounds

The conversion of the epoxide intermediate was achieved in a manner identical to that described in Example 1 (ii) except that instead of adjusting the pH of the aqueous phase with sulphuric acid there was used phosphoric acid (H$_3$PO$_4$) (40% w/w) (12g). $^{13}$C and $^1$H NMR analysis showed that PIB ketone had been selectively formed.

EXAMPLE 3

(i) Production of epoxide intermediate

The procedure of Example 1 (i) was repeated except that instead of using seven aliquots of 8% w/w H$_2$O$_2$ there was used seven aliquots of H$_2$O$_2$ (35% w/w) at hourly intervals (7×3.33g=23.31g; 0.24 mole) and only 100g toluene was used instead of 120g.

(ii) Conversion of epoxide intermediate to carbonyl-containing compounds

The conversion of the epoxide intermediate was achieved in a manner identical to that described in Example 1 (ii) except that instead of adjusting the pH of the aqueous phase with sulphuric acid there was used nitric acid (70% w/w) (0.5g) and instead of using seven aliquots of 8% w/w H$_2$O$_2$ there was used seven aliquots of 35% w/w H$_2$O$_2$ (7×3.33g =23.31g; 0.24 mole). IR analysis of the product confirmed by $^{13}$C and $^1$H NMR showed that the product was a mixture of mainly PIB alcohol together with small amounts of aldehyde and carboxylic acid.

EXAMPLE 4

(i) Production of PIB intermediate

The procedure of Example 3 (i) was repeated.

(ii) Conversion of epoxide intermediate to carbonyl-containing compounds

The conversion of the epoxide intermediate was achieved in a manner identical to that described in Example 1 (ii) except that instead of adjusting the pH of the aqueous phase with sulphuric acid there was used a mixture of phosphoric acid (40% w/w) (1g) and sulphuric acid (30% w/w) (3.2g) and instead of using seven aliquots of 8% w/w H$_2$O$_2$ there was used seven aliquots of 35% w/w H$_2$O$_2$ (7×3.33g=23.31g; 0.24 mole). IR analysis, $^{13}$C NMR and $^1$H NMR showed the product to be a mixture of PIB aldehydes and PIB ketones.

EXAMPLE 5—Production of nitrogen-containing material from PIB carbonyl

Into a 500ml flask fitted with a reflux coolant, heating mantle and thermocouple were charged the PIB oxidate product of Example 1. The PIB oxidate (96g; 0.1 mole) was heated to 80° C. and dimethylaminopropylamine (DMAPA) (0.4 mole) was added to the reaction flask.

The mixture was heated to 160° C. and further DMAPA (20g) was added. After distillation a slight vacuum (10 inches Hg) was applied to remove excess amine. The reaction mixture was cooled to 90° C. and xylene (100g) and butanol (90g) was added to the reaction vessel. Sodium borohydride (1.5g) was added over one hour. The excess sodium borohydride was then destroyed by adding small amounts of water carefully to the reaction mixture. The product was washed 6 times with water, separated and the organic layer thereby obtained was dried with anhydrous magnesium sulphate. Finally the solvent was removed by rotary evaporation.

The nitrogen content of the PIB DMAPA was evaluated using the Kjedhal method. It was found to be 0.95%.

EXAMPLE 6

Production of nitrogen-containing material from PIB carbonyl

The procedure of Example 5 was repeated except that instead of using the PIB oxidate product of Example 1 there was used the PIB oxidate product of Example 2.

The nitrogen content of the PIB DMAPA product by the Kjedhal method was found to be 0.75%.

We claim:

1. A process for converting epoxides to the corresponding carbonyl-containing compounds which process comprises reacting the epoxide with an oxidising agent in a liquid aqueous/organic two-phase system, which system comprises:
   (a) an organic phase substantially containing the epoxide and
   (b) an aqueous acidic phase substantially containing the oxidising agent, in the presence of an onium compound capable of achieving phase partitioning and a catalytic system comprising a first catalyst component which is at least one element selected from tungsten, molybdenum, vanadium and chromium, or a compound containing at least one of the aforesaid elements, and a second catalyst component which is a phosphorus (V) acid or a species convertible to a phosphorus (V) acid.

2. A process according to claim 1 wherein the oxidising agent is hydrogen peroxide.

3. A process according to either claim 1 or claim 2 wherein the epoxide is a polyisobutene (PIB) epoxide containing upwards of 30 carbon atoms.

4. A process according to claim 3 wherein the PIB is a high vinylidene PIB.

5. A process according to any one of 1 or 2 wherein the first catalyst component is tungsten or a tungsten-containing compound.

6. A process according to any one of 1 or 2 wherein the second catalyst component is phosphoric acid.

7. A process according to any one of 1 or 2 wherein the epoxide is reacted with the oxidising agent at a temperature in the range from 50° to 100° C.

8. A process according to any one of claims 2 to 7 wherein the aqueous phase is acidified with sulphuric acid, the epoxide is a PIB epoxide and a PIB aldehyde is selectively formed.

* * * * *